(12) United States Patent
Wilmink

(10) Patent No.: US 7,783,056 B2
(45) Date of Patent: Aug. 24, 2010

(54) EARPLUG

(75) Inventor: Engbert Wilmink, Delft (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 783 days.

(21) Appl. No.: 10/577,809

(22) PCT Filed: Oct. 28, 2004

(86) PCT No.: PCT/NL2004/000757

§ 371 (c)(1),
(2), (4) Date: Apr. 28, 2006

(87) PCT Pub. No.: WO2005/041831

PCT Pub. Date: May 12, 2005

(65) Prior Publication Data

US 2007/0086599 A1      Apr. 19, 2007

(30) Foreign Application Priority Data

Oct. 30, 2003   (EP)   .................................. 03078422

(51) Int. Cl.
*A61F 11/06* (2006.01)
*H04R 1/10* (2006.01)
*H04R 25/00* (2006.01)
*H04R 25/02* (2006.01)

(52) U.S. Cl. ........................... 381/72; 381/74; 381/380; 181/130

(58) Field of Classification Search .................... 381/72, 381/74, 380, 312–314, 375, 151; 181/130–135; 128/867
See application file for complete search history.

(56) References Cited

U.S. PATENT DOCUMENTS

| 4,651,777 | A | * | 3/1987 | Hardman | .................. 137/487.5 |
| 5,631,965 | A | * | 5/1997 | Chang et al. | .................. 381/72 |
| 5,832,094 | A | * | 11/1998 | Le Her | .................. 381/328 |
| 6,082,485 | A | * | 7/2000 | Smith | .................. 181/135 |
| 7,039,195 | B1 | * | 5/2006 | Svean et al. | .................. 381/71.6 |

FOREIGN PATENT DOCUMENTS

| FR | 2 657 716 A | 8/1991 |
| FR | 2 766 700 A | 2/1999 |
| WO | WO 02/17837 A | 3/2002 |

OTHER PUBLICATIONS

International Search Report, Dec. 16, 2004.

* cited by examiner

*Primary Examiner*—Devona E Faulk
(74) *Attorney, Agent, or Firm*—Leydig, Voit & Mayer, Ltd.

(57) ABSTRACT

Earplug comprising a plug member for blocking a man's ear canal, said plug member comprising at least one acoustic channel for channeling incoming acoustic energy to said man's ear. According to the invention, a detector for detecting an acoustic energy level or for detecting a control signal that is indicative for an acoustic energy level to be received, an acoustic valve positioned in said channel, and a control unit that, in response to said detector, controls said valve so as to attenuate the acoustic energy channeled through said acoustic channel.

17 Claims, 2 Drawing Sheets

EARPLUG

FILED OF THE INVENTION

The invention relates to an earplug comprising a plug member for blocking a person's ear canal, said plug member comprising at least one acoustic channel for channelling incoming acoustic energy into said person's ear.

BACKGROUND

In the context of this description, the word "ear" is taken to refer to the entire organ, consisting of the outer ear, the ear canal, the mid-ear and the inner ear. Human sound perception takes place in the inner ear and protection from hearing damage can be provided by attenuating sound as it travels through the ear canal, before it reaches the mid-ear.

In the field of hearing protection, an ear plug is commonly used to provide this attenuation. Generally, hearing protection is useful in noisy environments, for instance, for ground personnel in airports etc. It becomes essential, and is often required by law, in environments with noise levels above 80 dB. Also, in sub 80 dB environments, hearing protection can increase the comfort level, for instance when exposed to noise levels above 65 dB for longer periods of time.

In addition to providing protection against deafening or unpleasant noise levels, conventional hearing protectors may also block essential information such as voice communication, warning signals etc, even to such an extent that a protected person becomes uneasy wearing the protectors and decides to discontinue their use, potentially causing discomfort or hearing damage. To overcome these problems, various approaches have been suggested. Among these, European patent publication EP0333298 discloses an acoustic plug where a user can adjust the attenuation level by an adjustable insert that is placed in the acoustic channel. This ear plug needs to be manually adjusted by the user, by selecting and placing an insert with the desired amount of attenuation. In practical use, this ear plug essentially provides protection with fixed amount of attenuation, since a user will or cannot adjust instantaneously to variations in noise level. The present invention aims to provide an improved ear plug, offering a continuously, automatically adjusted amount of attenuation to adequately attenuate excessive noise levels while optimizing the perception of relevant sounds.

SUMMARY OF THE INVENTION

This object is attained by an ear plug according to claim 1. In particular, by providing a detector to assess the incident noise level and/or to register a control signal that is indicative for imminent variations in noise level, an acoustic valve in said channel can be controlled so that the perceived noise levels are effectively attenuated. In the latter case, the attenuation may adapted in advance in response to said control signal, so as to provide even further protection from hearing damage while maintaining optimum perception of desired signals.

Meanwhile, in less noisy environments, the attenuation is reduced automatically to improve the perception of voice communication, warnings or other relevant signals. Generally, at noise levels above 80 dB, the attenuation will automatically be increased to maintain a desired exposure level (e.g.) up until the maximum capability of the plug. Generally, said detector comprises a microphone.

In a preferred embodiment, said detector is positioned on the mid-ear side of the acoustic valve. For the detector, this provides protection, as well as a realistic registration of the remaining noise level perceived by the person. Also, accidental leakage through secondary channels may be automatically compensated for. Further, preferably, said valve comprises a valve seat and a valve member, wherein the valve member is actuated by the control unit and wherein the valve seat comprises a body of micro-channels. In practical embodiments, the physical volume for transmitting acoustic energy can be kept very small, for example, in an embodiment of a 4 mm acoustic channel, where the body of micro-channels comprises a wiring mesh. The free area of the channel may be reduced to 75% or more. The bulk of the incident acoustic energy is propagated directly through the air, and by effectively reducing the free (unobstructed) area of the acoustic channel, attenuation can be effectively realized. Furthermore, the acoustic channel can be realized in such a shape as to provide natural sound coloring in a much easier way than is possible by transmission of the acoustic signal via electronic means. In a further preferred embodiment, the valve member comprises a flexible foil closing said valve seat. The flexibility of the foil may be used to provide an acoustic valve that is at a predetermined attenuating position when said control unit is inactive. The flexible foil substantially blocks the direct sound transmission via the air. Said valve seat and said valve member may each comprise an electrode for providing electrostatic attraction. In the flexible foil configuration, the foil is then used as a capacitive element that is attracted to the valve seat by an electrostatic force. Here the foil is arranged to be electrically isolated from the valve seat, in particular from the wiring mesh. In one embodiment the foil comprises an electrically insulating layer provided on a metal layer.

In another embodiment, the valve is actuated by a piezo-element.

One preferential embodiment is an earplug wherein said acoustic valve and said detector are comprised in a modular housing that is insertable in the acoustic channel of said plug member. In such a way, the plug member may be manufactured separately, either in bulk or custom fitted. The acoustic valve may be interchanged as a modular unit.

The invention further relates to a modular housing to be fitted in an acoustic channel of an ear plug, comprising a detector for detecting an acoustic energy level or for detecting a control signal that is indicative for an acoustic energy level to be received, and an acoustic valve to be positioned in said channel, further comprising a control unit that, in response to said detector, controls said valve so as to attenuate the acoustic energy channeled through the acoustic channel.

BRIEF DESCRIPTION OF THE DRAWINGS

The invention will further be elaborated with reference to the annexed drawing. In the drawing.

DETAILED DESCRIPTION OF THE DRAWINGS

Figure 1:
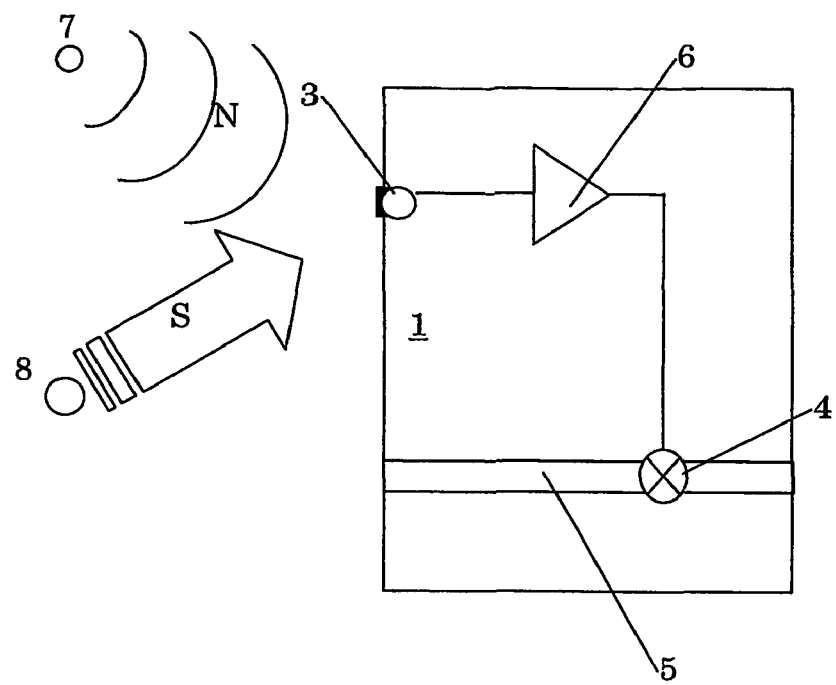
FIG. 1 shows the working principle of the acoustic valve according to the invention.

In the figure the same or corresponding elements will be referenced by the same reference numerals.

Figure 2:
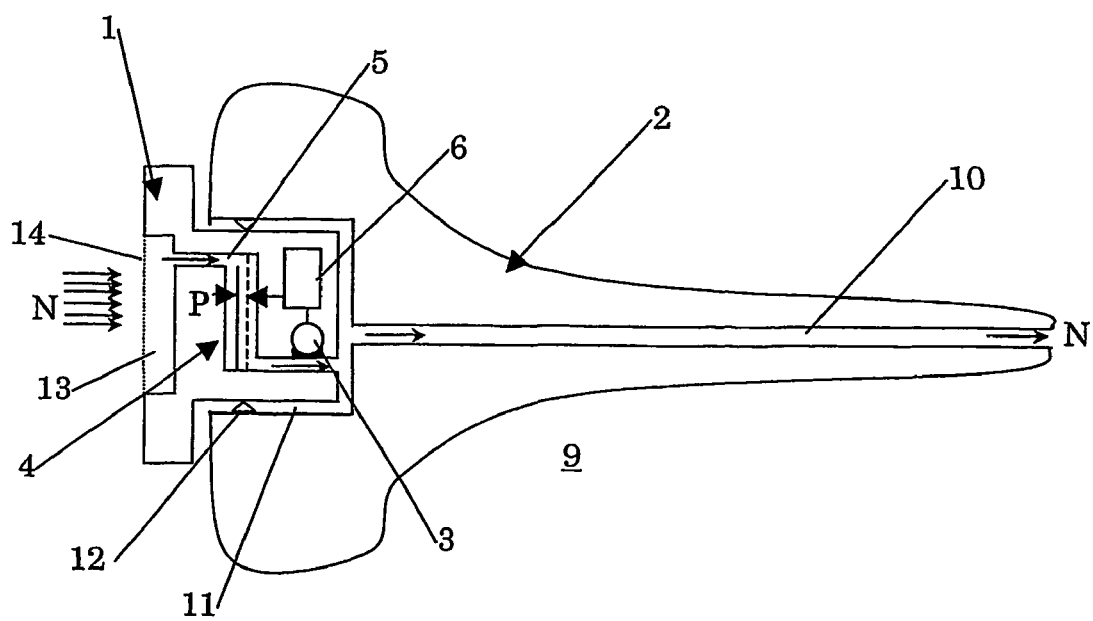
FIG. 2 shows an ear plug according to the invention.

In FIG. 1 the working principle of the acoustic valve of the invention is illustrated. The earplug is not illustrated here; only the modular housing 1 is schematically shown. In FIG. 2 is illustrated how the modular housing 1 may be inserted in an earplug member 2.

The modular housing comprises a microphone 3 and an acoustic valve 4 positioned in an acoustic channel 5. In response to the microphone 3, the acoustic valve 4 is actuated between a pass-through position with low attenuation and an attenuating position. In the latter position, the sound transmitted through channel 5 may ultimately be blocked substantially. The acoustic valve 4 is actuated by a control-unit 6, that controls said valve 4 in response to acoustic level sensed by said microphone 3. Said acoustic level is schematically indicated as "N", coming from source 7 that creates acoustic noise. In addition, a signal source 8 may be present, in particular an acoustic signal source, that creates a signal "S" that is picked up by the microphone 3. In case another type of signal is used, for instance a radio signal or similar, the modular housing is provided with an appropriate microphone for picking up said signal. The signal "S" may provide information that controls the acoustic valve, irrespective of a sensed acoustic level.

The earplug 9 that is illustrated in FIG. 2 may be an otoplastic (custom shaped to fit a person's ear canal) or a general elongated shape that substantially corresponds to an "average" person's ear canal. In the latter case, the elongated shape may be provided with side flaps (not shown) to adapt the plug to an individual ear canal. Generally, plug member 9 substantially blocks the ear canal except for a well-defined acoustic channel 10 provided in said plug member. Sound will therefore not reach the mid-ear unless through channel 10. The plug member 9 comprises a receiving cavity 11 for receiving a housing 1. The housing 1 is fitted in the cavity 11 by sealing member 12 so that sound (Indicated by arrows "N") can pass exclusively via the channel 5 provided in the modular housing 1, which is acoustically connected to the channel 10 of the ear plug member 9. The channel 5 comprises an inlet 13, which may be protected by an acoustically transparent cover 14. In the channel 5, an acoustic valve 4 is present. The valve 4 can be actuated (schematically indicated by arrows P) by a control unit 6 that controls the valve 4 in response to an acoustic level sensed by microphone 3. The housing 1 may further comprise a battery cell (not shown) for supplying the control unit 6, the valve 4 and the microphone 3. In the embodiment shown in FIG. 2, the microphone 3 is positioned downstream of the acoustic valve 4 to provide easier and more reliable indication of the noise level that is actually perceived by a person.

Figure 3:
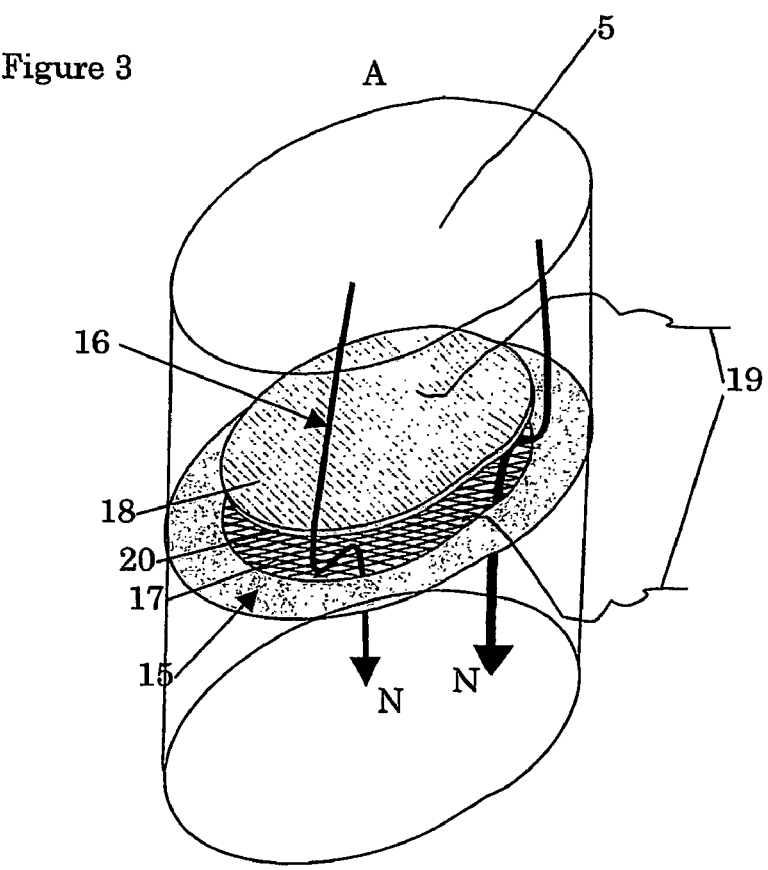
FIGS. 3 A and 3 B show two embodiments of an acoustic valve according to the invention.
Figure 3:
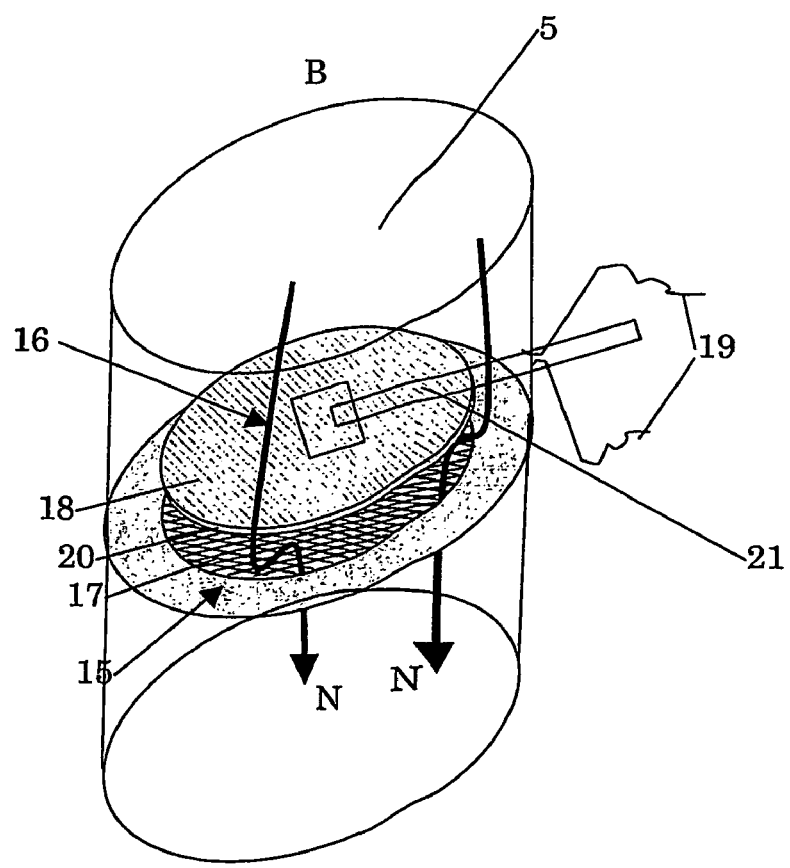

In FIG. 3A, an embodiment is shown of an acoustic valve 4 according to the invention. Here, the valve comprises a valve seat 15 and a valve member 16 positioned in an acoustic channel 5 having a general diameter of, for instance, half a centimeter. The valve seat 15 comprises a body of microchannels, for instance, a wiring mesh 17 having openings of a few micrometer (10-50 micrometer). Such a wiring mesh 17 can be effectively blocked by an elastic foil 18 that is pushed onto the mesh 17. In the embodiment shown this is done by electrostatic force. The foil 18 is maintained in a predetermined position relative to the mesh 17 by mechanical means, such as for instance brackets (not shown) or a ring shape allowing the passage of sound. Electrodes 19 are provided onto the foil 18 and the wiring mesh 17 for applying the electrostatic field. Generally, the mesh 17 will consist of an electric conductive material, such a Ni or Sn. The foil 18 may be a plastic foil, that is coated by a metallic layer. In this respect, the plastic layer may serve as a dielectric 20. Alternatively, the foil 18 may be an electret that moves through an applied electrostatic field. Due to the flexibility, the foil 18 is acoustically transparent when not pushed against the wiring mesh 17. Furthermore, through the flexibility of the foil, the foil is maintained at a predetermined distance to the wiring mesh 6 when the electrostatic force is absent due to absent electric voltage on the electrodes 19. This reduces the power requirements, so the ear plug can be operated long-term without need for battery replacement.

In the embodiment shown in FIG. 3B, the valve member is actuated by piezo-force relative to the wiring mesh 17, through a piezo element 21 that is provided on the valve member 18. Here, the valve member 18 does not need to be electrically insulated from the wiring mesh. The propagation of the bulk of the sound is shown by arrows N. Although some sound may be transmitted by the foil as well, this quantity is minor in comparison with the transmission via the direct air path that is provided between the foil 18 and the mesh 20. Hence, when this direct air path is closed by pushing the foil 18 against the mesh 20, the sound transmission through the acoustic channel 5 is effectively blocked.

Although the invention has been illustrated with reference to the drawing, the invention is not limited thereto but may comprise various modifications and variations without departing from the scope of the invention. In this respect, for instance, the acoustic channel may comprise a filter that enhances or reduces transmission of sound in certain frequency bands. Such a filter may be provided through specific dimensioning and shaping of the acoustic channel. A further microphone may be present to detect the control signal, such as an antenna circuit or the like. Alternatively, the microphone may be adapted for receiving control signals. Such modifications are considered to fall within the scope as defined in the following claims.

The invention claimed is:

1. An earplug comprising:
   a plug member for blocking a person's ear canal, said plug member comprising at least one acoustic channel for channeling incoming acoustic energy into said person's ear;
   a detector for detecting an acoustic energy level or for detecting a control signal that is indicative of an acoustic energy level to be received;
   an acoustic valve positioned in said acoustic channel; and
   a control unit that, in response to an acoustic level sensed by said detector, controls actuation of said acoustic valve between a pass-through position with a low attenuation and an attenuating position;
   wherein said valve comprises a valve seat and a valve member, wherein the valve member is actuated by the control unit and wherein the valve seat comprises a body of micro-channels.

2. The earplug according to claim 1, wherein the body of microchannels comprises a wiring mesh.

3. The earplug according to claim 1, wherein the valve member comprises a flexible foil closing said valve seat.

4. The earplug according to claim 1, wherein said valve seat and said valve member each comprise an electrode for providing electrostatic attraction.

5. The earplug according to claim 1, wherein at least one of either the valve seat and/or valve member are actuated by a piezo-element.

6. The earplug according to claim 1, wherein, said valve is maintained at a specified attenuating position when said control unit is inactive.

7. The earplug according to claim 1, wherein said acoustic valve and said detector are comprised in a modular housing that is insertable in the acoustic channel of said plug member.

8. The earplug according to claim 1, wherein the control signal is an acoustic signal.

9. The earplug according to claim 1, wherein said detector comprises a microphone.

10. A modular housing to be fitted in an acoustic channel of an ear plug, the modular housing comprising:
- a detector for detecting an acoustic energy level or for detecting a control signal that is indicative for an acoustic energy level to be received;
- an acoustic valve to be positioned in said channel; and
- a control unit that, in response to an acoustic level sensed by said detector, controls actuation of said acoustic valve between a pass-through position with low attenuation and an attenuating position;
- wherein said valve comprises a valve seat and a valve member, wherein the valve member is actuated by the control unit and wherein the valve seat comprises a body of micro-channels.

11. The modular housing according to claim 10, wherein said detector is positioned on a mid-ear side of the acoustic valve.

12. The modular housing according to claim 10, wherein the body of micro-channels comprises a wiring mesh.

13. The modular housing according to claim 10, wherein the valve member comprises a flexible foil closing said valve seat.

14. The modular housing according to claim 10, wherein said valve seat and said valve member each comprise an electrode for providing electrostatic attraction.

15. The modular housing according to claim 10, wherein at least one of either the valve seat and/or valve member are actuated by a piezo-element.

16. The modular housing according to claim 10, wherein, said valve is maintained at a specified attenuating position when said control unit is inactive.

17. The modular housing according to claim 10, wherein said detector comprises a microphone.

* * * * *